United States Patent
Pratt et al.

(10) Patent No.: US 10,813,869 B2
(45) Date of Patent: Oct. 27, 2020

(54) AQUEOUS OXIDIZING COMPOSITION

(71) Applicant: KAO GERMANY GMBH, Darmstadt (DE)

(72) Inventors: Dominic Pratt, Darmstadt (DE); Niu Jian, Darmstadt (DE)

(73) Assignee: KAO GERMANY GMBH, Darmstadt (DE)

( * ) Notice: Subject to any disclaimer, the term of this patent is extended or adjusted under 35 U.S.C. 154(b) by 0 days.

(21) Appl. No.: 15/540,659

(22) PCT Filed: Dec. 11, 2015

(86) PCT No.: PCT/EP2015/079358
§ 371 (c)(1),
(2) Date: Jun. 29, 2017

(87) PCT Pub. No.: WO2016/107727
PCT Pub. Date: Jul. 7, 2016

(65) Prior Publication Data
US 2017/0360670 A1  Dec. 21, 2017

(30) Foreign Application Priority Data
Dec. 29, 2014 (EP) .................. 14200458

(51) Int. Cl.
| A61K 8/60 | (2006.01) |
| A61Q 5/08 | (2006.01) |
| A61Q 5/10 | (2006.01) |
| A61K 8/86 | (2006.01) |
| A61K 8/39 | (2006.01) |
| A61K 8/19 | (2006.01) |
| A61K 8/22 | (2006.01) |
| A61K 8/23 | (2006.01) |
| A61K 8/24 | (2006.01) |
| A61K 8/25 | (2006.01) |
| A61K 8/31 | (2006.01) |
| A61K 8/41 | (2006.01) |
| A61K 8/46 | (2006.01) |
| A61K 8/49 | (2006.01) |
| A61K 8/73 | (2006.01) |
| A61K 8/96 | (2006.01) |

(52) U.S. Cl.
CPC ............... $A61K$ 8/60 (2013.01); $A61K$ 8/19 (2013.01); $A61K$ 8/22 (2013.01); $A61K$ 8/23 (2013.01); $A61K$ 8/24 (2013.01); $A61K$ 8/25 (2013.01); $A61K$ 8/31 (2013.01); $A61K$ 8/39 (2013.01); $A61K$ 8/41 (2013.01); $A61K$ 8/416 (2013.01); $A61K$ 8/463 (2013.01); $A61K$ 8/498 (2013.01); $A61K$ 8/4926 (2013.01); $A61K$ 8/4946 (2013.01); $A61K$ 8/731 (2013.01); $A61K$ 8/86 (2013.01); $A61K$ 8/965 (2013.01); $A61Q$ 5/08 (2013.01); $A61Q$ 5/10 (2013.01); $A61K$ 2800/4324 (2013.01); $A61K$ 2800/882 (2013.01)

(58) Field of Classification Search
CPC .... A61K 2800/4324; A61K 8/19; A61K 8/22; A61K 8/23; A61K 8/24; A61K 8/25; A61K 8/31; A61K 8/41; A61K 8/416; A61K 8/463; A61K 8/4926; A61K 8/4946; A61K 8/498; A61K 8/60; A61K 8/731
See application file for complete search history.

(56) References Cited

U.S. PATENT DOCUMENTS

| 2,313,027 | A | 3/1943 | Schueller | |
| 4,788,052 | A * | 11/1988 | Ng | A61K 8/042 424/53 |
| 4,839,156 | A * | 6/1989 | Ng | A61K 8/042 424/53 |
| 6,582,477 | B1 | 6/2003 | Plos | |
| 2004/0221400 | A1 | 11/2004 | Cotteret et al. | |
| 2006/0088485 | A1* | 4/2006 | Ishida | A61K 8/4973 424/62 |
| 2010/0098645 | A1* | 4/2010 | Barrett | A61K 38/443 424/61 |
| 2010/0154143 | A1 | 6/2010 | Guerin et al. | |
| 2010/0158844 | A1 | 6/2010 | Braida-Valerio | |

FOREIGN PATENT DOCUMENTS

| DE | 10 2011 085173 A1 | 7/2012 | | |
| EP | 1 043 012 A2 | 10/2000 | | |
| EP | 2 559 456 A2 | 2/2013 | | |
| FR | 2 966 721 A1 | 5/2012 | | |
| FR | 2 966 726 A1 | 5/2012 | | |
| GB | 2 476 217 A | 6/2011 | | |
| JP | 2001-002537 | * | 9/2001 | ............ A61K 8/00 |
| JP | 2008 308442 A | | 12/2008 | |
| JP | 2009-126795 | * | 6/2009 | ............ A61K 8/06 |
| WO | WO 2012/059406 A1 | * | 5/2012 | ............ A61K 8/02 |
| WO | WO 2012/059407 A1 | * | 5/2012 | ............ A61K 8/41 |
| WO | WO 2014/025355 A1 | * | 2/2014 | ............ A61K 8/24 |

OTHER PUBLICATIONS

International Search Report dated May 31, 2016, dated Jun. 15, 2016.

* cited by examiner

Primary Examiner — Aradhana Sasan
(74) Attorney, Agent, or Firm — Norris McLaughlin, P.A.

(57) ABSTRACT

The present invention relates to an aqueous oxidizing composition comprising one or more oxidizing agent, one or more sugar and/or one or more polyethylene glycol and having a pH in the range of 1 to 5.

11 Claims, No Drawings

AQUEOUS OXIDIZING COMPOSITION

This application is the U.S. National Stage of International Application No. PCT/EP2015/079358, filed Dec. 11, 2015, which claims foreign priority benefit under 35 U.S.C. § 119 of European Application No. 14200458.9 filed Dec. 29, 2014.

The present invention relates to an aqueous oxidizing composition comprising one or more oxidizing agent and one or more sugar and/or one or more polyethylene glycol.

Oxidizing compositions have been used for bleaching keratin fibers especially human hair in various chemical environments. The bleaching, also called lightening within the meaning of the present specification, power is dependent on pH but also dependent on additional compounds in such compositions. It has been known that bleaching effect of an oxidizing composition does not exist at all or at a very low, negligible extend at neutral to acidic pH ranges but high level of colour bleaching is achieved at alkaline pH's especially strong alkaline pH values in the range of 9 to 12. Additionally, other ingredients may affect the bleaching effect of an oxidizing composition.

It has also been the aim of the product development teams for ages to improve bleaching power of aqueous oxidizing composition without altering the mildness of the composition and also without elevating the bleaching active ingredient content of the composition. In recent years addition of buffering salts has been proposed. However, the level of bleaching achieved is still not satisfactory and, therefore, requires further improvement.

The inventors of the present invention have unexpectedly found out that addition of sugar and alike compounds and/or polyethylene glycols into an aqueous oxidizing composition comprising one or more oxidizing agent bleaches human hair more effectively and lighter colors and colorations may be achieved using the composition.

Accordingly the first object of the present invention is an aqueous composition comprising one or more oxidizing agent, one or more mono and/or disaccharide and/or one or more compound according to the general structure

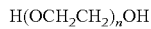

wherein n is in the range of 4 to 800, and has a pH in the range of 1 to 5.

The second object of the present invention is the use of the composition for bleaching hair.

The third object is a process for bleaching hair wherein the aqueous oxidizing composition of the present invention is mixed with a composition comprising one or more alkalizing agent and is applied onto hair and after leaving on the hair for 1 to 60 min rinsed off from hair and hair is optionally shampooed and dried with a hair drier.

The fourth object is a process for bleaching hair wherein the aqueous oxidizing composition of the present invention is mixed with anhydrous composition comprising one or more persalt and one or more alkalizing agent and is applied onto hair and after leaving on the hair for 1 to 60 min rinsed off from hair and hair is optionally shampooed and dried with a hair drier.

The fifth object is a process for coloring hair wherein the aqueous oxidizing composition of the present invention is mixed with a composition comprising one or more alkalizing agent and one or more hair dye and is applied onto hair and after leaving on the hair for 1 to 60 min rinsed off from hair and hair is optionally shampooed and dried with a hair drier.

The composition of the present invention comprises one or more oxidizing agent. The suitable once are hydrogen peroxide, urea peroxide, melamin peroxide or perborate salts. One or more oxidizing agent is comprised in the aqueous compositions at a total concentration in the range of 0.1 to 25%, preferably 0.5 to 20% and more preferably 1 to 15% by weight, calculated to the total of the composition.

Composition of the present invention has an acidic pH, between 1 and 5, preferably between 1.5 and 4.5, more preferably between 2 and 4, and most preferably between 2.5 and 3.5. The pH of the compositions is adjusted by using commonly used organic and/or inorganic acids, preferably with inorganic acids and their salts and more preferably with phosphoric acid and its salts.

The compositions comprise one or more saccharide selected from monosaccharides and disaccharides. The suitable monosaccharides are glucose, fructose, mannose, rhamnose, ribose and xylose and suitable disaccharides are lactose, lactulose, maltose, mellibiose, sucralose, sucrose, trehalose and xylobiose. Preferred are glucose, fructose, mannose, lactose, maltose, sucrose and trehalose. More preferred are glucose, fructose, lactose, sucrose and trehalose. The most preferred are sucrose and trehalose. Sucrose is in particular preferred disaccharide.

The composition comprises one or more compound according to above given general structure wherein n is preferably 6 to 500, more preferably 10 to 200 and most preferably 14 to 150. Preferably one or more compound of the above given general structure is selected from PEG-4, PEG-6, PEG-7, PEG-8, PEG-9, PEG-10, PEG-12, PEG-14, PEG-16, PEG-18, PEG-20, PEG-32, PEG-33, PEG-40, PEG-45, PEG-55, PEG-60, PEG-75, PEG-80, PEG-90, PEG-100, PEG-135, PEG-150, PEG-180, PEG-200, PEG-220, PEG-240, PEG-300, PEG-400, PEG-450, PEG-500 and PEG-800. Preferred are PEG-6, PEG-7, PEG-8, PEG-9, PEG-10, PEG-12, PEG-14, PEG-16, PEG-18, PEG-20, PEG-32, PEG-33, PEG-40, PEG-45, PEG-55, PEG-60, PEG-75, PEG-80, PEG-90, PEG-100, PEG-135, PEG-150, PEG-180, PEG-200, PEG-220, PEG-240, PEG-300, PEG-400, PEG-450 and PEG-500, more preferred are PEG-10, PEG-12, PEG-14, PEG-16, PEG-18, PEG-20, PEG-32, PEG-33, PEG-40, PEG-45, PEG-55, PEG-60, PEG-75, PEG-80, PEG-90, PEG-100, PEG-135, PEG-150, PEG-180 and PEG-200, most preferred are PEG-14, PEG-16, PEG-18, PEG-20, PEG-32, PEG-33, PEG-40, PEG-45, PEG-55, PEG-60, PEG-75, PEG-80, PEG-90, PEG-100, PEG-135 and PEG-150. PEG-20, PEG-32, PEG-33, PEG-40, PEG-45, PEG-55 and PEG-60 are particularly preferred.

The composition comprising one or more mono or disaccharide and/or a compound according to the above general structure at a total concentration in the range of 1 to 60%, preferably 5 to 55%, more preferably 10 to 50% and most preferably 15 to 50% by weight, calculated to the total of the composition.

The two compositions comprising the carboxylic acid are aqueous compositions and may be in the form of a solution, emulsion, cream, gel and mousse.

Compositions of the present invention are preferably emulsions and comprise therefore fatty alcohol, oil and surfactants as emulsifiers.

The fatty alcohols preferred are according to the following general structure

wherein $R_1$ is a linear or branched, saturated or unsaturated alkyl chain with 12 to 22 C atoms. Suitable fatty alcohols are myristyl alcohol, cetyl alcohol, stearyl alcohol and behenyl alcohol and their mixtures. Most preferred is the mixture of cetyl and stearyl alcohol also known as cetearyl alcohol.

The concentration of one or more fatty alcohols is in the range of 1 to 25%, preferably 1 to 20%, more preferably 1.5 to 15% and most preferably 1.5 to 10% by weight calculated to total composition.

Compositions comprise preferably oil, more preferably natural oil and most preferably natural triglycerides. Concentration of oil varies between 0.1 and 25%, preferably 0.5 and 25% and more preferably 1 and 20%, most preferably 2 and 20%, in particular 2.5 and 15% by weight calculated to the total composition.

Suitable natural triglycerides are argan oil, shea butter oil, karite oil, olive oil, almond oil, avocado oil, ricinus oil, coconut oil, palm oil, sesame oil, peanut oil, sunflower oil, peach kernel oil, wheat germ oil, macadamia nut oil, macadamia oil, night primrose oil, jojoba oil, castor oil, soya oil, lanolin, passiflora oil, black cumin oil, borage oils, grapeseed oil, hempseed oil, kukui nut oil, and rosehip oil. Preferred are argan oil, shea butter oil, karite oil, olive oil, almond oil, avocado oil, ricinus oil, coconut oil, palm oil, sesame oil, peanut oil, whale oil, sunflower oil, peach kernel oil, wheat germ oil, macadamia nut oil, macadamia oil, night primrose oil, jojoba oil, castor oil, and soya oil. More preferred are argan oil, shea butter oil, karite oil, macadamia nut oil, macadamia oil, olive oil, almond oil, avocado oil, ricinus oil, coconut oil, palm oil, sesame oil, peanut oil, sunflower oil, peach kernel oil, wheatgerm oil, jojoba oil, castor oil, and soya oil. Most preferred are argan oil, shea butter oil, karite oil, olive oil, almond oil, avocado oil, coconut oil, macadamia nut oil, macadamia oil, palm oil, sesame oil, peach kernel oil, wheatgerm oil, jojoba oil, and soya oil. Particularly preferred are argan oil, shea butter oil and karite oil which may be comprised as a single oil component or in admixture with each other.

Further suitable oil components are natural oils such as paraffin oil.

Further suitable ones are synthetic oils such as silicones known with CTFA adopted name dimethicone, cyclomethicone, and arylates silicones such as phenyl trimethicone which are available commercially from Dow Corning.

Further suitable synthetic oils are fatty acid fatty alcohol esters such as octyl palmitate, isocetyl palmitate, isopropyl palmitate and octyl stearate.

Compositions preferably comprise one or more surfactants as an emulsifier. Suitable surfactants are non-ionic, cationic and anionic ones and their mixtures.

Anionic surfactants suitable within the scope of the invention are in principal known from the cleansing compositions These are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

It is also possible to use mixtures of several anionic surfactants. Preferred are alkyl sulphates or alkyl ether sulphates and the most preferred are alkyl ether sulphates.

Further surfactants in the compositions according to the invention are nonionic surfactants. Especially suited nonionic surfactants are, for example, long-chain fatty acid mono- and dialkanolamides, such as coco fatty acid mono- or diethanolamide and myristic fatty acid mono or diethanolamide, stearic acid mono or diethanolamide. Further nonionic surfactants suited are alkyl polyglucosides with an alkyl group of 8 to 18 carbon atoms, and with 1 to 5 glucoside units. Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics$^R$", as well as fatty alcohol ethoxylates. Further nonionic surfactants preferred in the compositions according to invention are $C_{10}$-$C_{22}$-fatty alcohol ethoxylates. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16":The average degree of ethoxylation thereby ranges between about 2.5 and about 25, preferably about 10 and about 20. The most preferred is ceteth, steareth and ceteareth with 20 to 35 ethoxy groups and ceteareth-30 is particularly preferred.

Compositions preferably comprise a cationic surfactant and especially a monoalkyl cationic surfactant according to the general structure

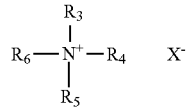

where $R_3$ is a saturated or unsaturated, branched or linear alkyl chain with 8-22 C atoms or

where $R_7$ is saturated or unsaturated, branched or linear alkyl chain with 7-21 C atoms and n has typical value of 1-4 or

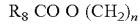

where $R_8$ is saturated or unsaturated, branched or linear alkyl chain with 7-21 C atoms and n has typical value of 1-4, and $R_4$, $R_5$ and $R_6$ are H or lower alkyl chain with 1 to 4 Carbon atoms, and X is typically chloride, bromide, methosulfate.

Typical examples of those ingredients are cetyl trimethyl ammonium chloride, stear trimonium chloride, palmitoyl trimonium chloride, stearamidopropyl trimonuim chloride and oleoylethyl trimethyl ammonium methosulfate. The most preferred are cetyl trimethly ammonium chloride, stear trimonium chloride and palmitoyl trimonium chloride. Cetyl trimethyl ammonium chloride is particularly preferred.

The concentration of one or more surfactants is in the range of 0.1 to 25%, preferably 0.2 to 20%, more preferably 0.5 to 15% and most preferably 1 to 10% by weight calculated to total composition.

The pH of the composition is in the range of 2 to 6, preferably 2 to 5, more preferably 2.5 to 4 and most preferably 2.5 to 3.5. The pH is measured with a widely used laboratory equipment and at ambient temperature, preferably at 20° C. pH of the compositions may be adjusted with organic and inorganic acids used widely in cosmetic composition. Preferred is phosphoric acid and/or its salts.

Compositions preferably comprise additionally one or more chelating agent. In principal any chelating agent known in the field of cosmetics is suitable for the compositions of the present invention. Preferred are ethylene diamine tetraacetic acid (EDTA) etidronic acid, galactaric acid, gluconic acid and therei respective salts. Most preferred are diamine tetraacetic acid (EDTA) etidronic acid and gluconic acid and their respective salts and also their mixtures.

The compositions may comprise one or more compound for stabilizing the peroxide. Suitable ones are salicylic acid and/or its salts, acetaminophen and oxyquinoline and/or its salts. Concentration or such compounds is in the range of of 0.001 to 1%, more preferably 0.002 to 0.75% most preferably 0.005 to 0.5% by weight calculated to the total composition.

For hair bleaching purposes, the composition of the present invention is mixed with another composition comprising one or more alkalizing agent prior to application onto hair. The suitable alkalizing agents are ammonia and a compound according to the general structure

wherein $R_9$, $R_{10}$ and $R_{11}$ are same or different H, $C_1$-$C_6$ alkyl, $C_1$-$C_6$ monohydroxyalkyl or $C_2$-$C_6$ polyhydroxyalkyl with the condition that at least one of $R_9$, $R_{10}$ and $R_{11}$ is a mono or polyhydroxyalkyl, preferably $R_9$, $R_{10}$ and $R_{11}$ are same or different H, $C_1$-$C_4$ alkyl, $C_1$-$C_4$ monohydroxyalkyl or $C_2$-$C_4$ polyhydroxyalkyl with the condition that at least one of $R_9$, $R_{10}$ and $R_{11}$ is a mono or polyhydroxyalkyl, more preferably $R_9$, $R_{10}$ and $R_{11}$ are same or different H, $C_2$-$C_4$ alkyl, $C_2$-$C_4$ monohydroxyalkyl or $C_2$-$C_4$ polyhydroxyalkyl with the condition that at least one of $R_9$, $R_{10}$ and $R_{11}$ is a mono or polyhydroxyalkyl, Suitable alkanolamines according to the general formula of above are monoethanolamine, diethanolamine, triethanolamine, monoethanol methylamine, monoethanoldimethylamine, di-ethanolmethylamine, monoethanolethylamine, monoethanoldiethylamine, diethanolethylamine, monoethanolpropylamine, monoethanoldipropylamine, diethanolpropylamine, monoethanolbutylamine and diethanolbutylamine.

Preferred are monoethanolamine, diethanolamine and triethanolamine. The most preferred is monoethanolamine.

The concentration of alkalizing agent in the composition varies between 1 and 35%, preferably 1 and 30, more preferably 2.5 and 25 and most preferably 2.5 to 20% by weight calculated to the total composition.

The alkaline composition can further comprise one or more hair dye in order to dye hair. The suitable dyes are direct dyes and oxidative dye precursors and coupling substances in combination with dye precursors.

Oxidative dyeing compositions comprise one or more oxidative dye precursor, also called developer. Suitable oxidative dyestuffs precursors are tetraaminopyrimidines, in particular 2,4,5,6-tetraaminopyrimidine and the lower alkyl derivatives thereof; suitable triaminohydroxypyrimidines are, for example 4-hydroxy-2,5,6-triaminopyrimidine, 2-hydroxy-4,5,6-triaminopyrimidine and 5-hydroxy-2,4,6-triaminopyrimidine; suitable mono- and diamino dihydroxy-pyrimidines are, for example, 2,6-dihydroxy-4,5-diaminopyrimidine, 2,4-diamino-6-hydroxy-pyrimidine or 4,6-dihydroxy-2,5-diaminopyrimidine or the water-soluble salts thereof, aminophenol derivatives such as 4-aminophenol, 4-amino-3-methylphenol, 2-chloro-4-aminophenol, 2,6-dichloro-4-aminophenol, 2,4-diamino-phenol, 2,6-dibromo-4-aminophenol and/or 2-aminophenol and water-soluble salts thereof, furthermore, phenylenedimanine derivatives such as 2,5-diamino-toluene, 2-n-propyl or 2-ethyl-p-phenylene-diamine, 2,6-dimethyl-p-phenylenediamine, 2-(2,5-diaminophenyl) ethanol, 1-amino -4-bis-(2'-hydroxy-ethyl) aminobenzene, 2-(2-hydroxyethyl amino)-5-aminotoluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethylamino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene or the water-soluble salts thereof, pyrazole derivatives such as 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 1-methyl-4,5-diaminopyrazole, 1-methylethyl-4,5-diaminopyrazole, 1-phenylmethyl-4,5-diaminopyrazole, 1-methyl-4,5-diaminopyrazole, 1-(4-methylphenyl)methyl-4,5-diaminopyrazole, 1-methyl-3-phenyl-4,5-diaminopyrazole and the water-soluble salts. The use of the above mentioned oxidative dye precursors as mixture is also customary in hair coloring area.

The total concentration of the oxidation dyestuff precursors and/or their water soluble salts customarily ranges between about 0.05% and 5%, preferably 0.1% and 4%, in particular 0.1% to 3% by weight, calculated to the total hair dyeing composition prior to mixing with oxidizing agent, whereby these figures are always related to the proportion of free base.

The composition according to the invention optionally comprises one or more coupling substance, which can be selected from resorcinol, 2-methyl resorcinol, 4-chlororesorcinol, 2-amino-4-chlorophenol, 5-amino-4-methoxy-2-methylphenol, 3-amino-phenol, 1-methyl-2-hydroxy-4-aminobenzene, 3-N,N-dimethyl aminophenol, 2.6-dihydroxy-3.5-dimethoxypyridine, 5-amino-3-methylphenol, 6-amino-3-methylphenol, 3-amino-2-methylamino-6-methoxypyridine, 2-amino-3-hydroxypyridine, 2-dimethyl-amino-5-aminopyridine, 2,6-diaminopyridine, 1,3-diamino-benzene, 1-amino-3-(2'-hydroxyethylamino)benzene, 1-amino-3-[bis(2'-hydroxyethyl) amino]benzene, α-naphthol, 4,6-dichlororesorcinol, 1,3-diamino-toluene, 1-hydroxy naphthalene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1.2-methyldioxy benzene, 2,4-diamino-3-chloro-phenol, 5-amino-2-methoxyphenol and/or 1-methoxy-2-amino-4-(2'-hydroxyethyl amino)benzene or the water-soluble salts thereof. However, this shall not exclude the addition of further developing and coupling substances. In the preferred embodiment of the present invention composition comprise additionally one or more coupling agent.

The weight proportion of the named developing substances to the coupling substances ranges between about 1:8 to 8:1, preferably about 1:5 to 5:1, in particular 1:2 to 2:1. In the hair dyeing compositions according to the invention, the coupling substance(s) as reaction partners of the developing substance(s) are present in approximately the same molecular proportions as the developing substances, i.e. in amounts from 0.01% to 5.0%, preferably 0.05% to 4%, in particular 0.1% to 3% by weight, calculated to the total composition prior to mixing with oxidizing agent, whereby these figures are always related to the proportion of free base.

The composition of the present invention can comprise additionally direct dyes of neutral, cationic and anionic character. Some examples to suitable cationic dyes are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 51, Basic Red 76, Basic Violet 1, Basic Violet 2, Basic Violet 3, Basic Violet 10, Basic Violet 14 and Basic Yellow 57. According to the invention, suitable cationic dyestuffs are in principal those any available on the market for cosmetic hair colouring applications. For this purpose, special reference is made to the PCT application WO 95/15144 of Ciba-Geigy AG. The content of the PCT application WO 95/15144 is by reference incorporated here.

Examples to suitable direct acting anionic dyes are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Some examples to those suitable neutral dyes (HC dyes), so called nitro dyes, are HC Blue No.2, HC Blue No.4, HC Blue No.5, HC Blue No.6, HC Blue No.7, HC Blue No.8, HC Blue No.9, HC Blue No.10, HC Blue No.11, HC Blue No.12, HC Blue No.13, HC Brown No.1, HC Brown No.2, HC Green No.1, HC Orange No.1, HC Orange No.2, HC Orange No.3, HC Orange No.5, HC Red BN, HC Red No.1, HC Red No.3, HC Red No.7, HC Red No.8, HC Red No.9, HC Red No.10, HC Red No.11, HC Red No.13, HC Red No.54, HC Red No.14, HC Violet BS, HC Violet No.1, HC Violet No.2, HC Yellow No.2, HC Yellow No.4, HC Yellow No.5, HC Yellow No.6, HC Yellow No.7, HC Yellow No.8, HC Yellow No.9, HC Yellow No.10, HC Yellow No.11, HC Yellow No.12, HC Yellow No.13, HC Yellow No.14, HC Yellow No.15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Plant dyestuffs can also be used alone or in combination with synthetic direct-acting dyestuffs, for example henna (red or black), alkanna root, laccaic acid, indigo, logwood powder, madder root and rhubarb powder, etc.

According to the invention, the coloring composition comprises direct hair dyes at a total concentration of 0.01 to 5%, preferably 0.05 to 3%, more preferably 0.1 to 2% by weight calculated to total composition excluding the oxidative composition.

The hair dyeing composition comprising one or more oxidative dye precursor according to the present invention can comprise an organopolysiloxane wherein at least one silicon atom is linked to an alkylene group having a heteroatom, in particular a nitrogen atom, with a poly-(N-acyl alkyleneimine) units of the formula

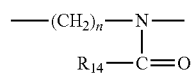

wherein n is a number from 1 to 5 and $R_{14}$ is hydrogen, a $C_1$-$C_{12}$-alkyl or cycloalkyl, aralkyl or aryl group.

Preferred organopolysiloxane polymers are those of the type disclosed in EP-A 640 643, in particular optionally quaternized aminoalkyl, in particular aminopropyl dimethyl polysiloxane/polyethyl oxazoline copolymers of the formula

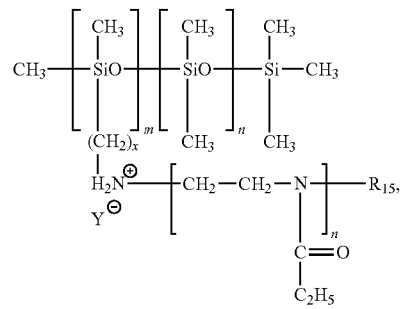

wherein m and n each are numbers from 20 to 10,000, in particular 50 to 7,000, especially 100 to 5,000, x is a number between 1 and 5, preferably 3, and y is a number from 5 to 30, $R_{15}$ is a $C_1$-$C_{12}$-alkyl or aryl group, in particular a methyl, ethyl or benzyl group, and $Y^-$ is an anion.

Especially suited are the organopolysiloxanes disclosed under the terms A-1, A-2 and A-3 on pages 12 to 13 of EP-A 640 643. The proportion of graft copolymers in the hair colouring compositions according to the invention ranges from 0.05% to 5%, preferably 0.1% to 2.5%, in particular 0.5% to 1.5% by weight, calculated to the total composition.

Another compound that may be comprised in the colouring composition comprising one or more oxidative dye precursor is a ceramide type of compounds according to the general formula

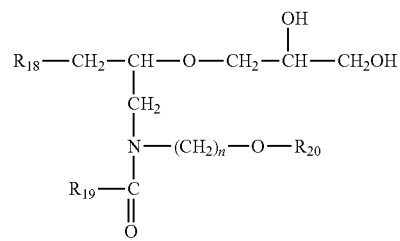

where $R_{18}$ and $R_{19}$ are independent from each other alkyl- or alkenyl group with 10 to 22 carbon atoms, $R_{20}$ is methyl, ethyl, n-propyl or isopropyl group and n is a number between 1 to 6, preferably 2 or 3. The concentration of the ceramide type of compound in colouring compositions of the present invention can be in the range of 0.01 to 2 and especially 0.01 to 1% by weight calculated to the total composition.

The compositions comprising one or more oxidative dye precursor according to the present invention can further comprise one or more ubiquinone of the formula.

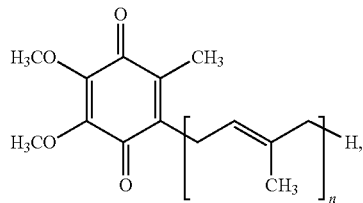

wherein n is a number from 1 to 10. The concentration of ubichinones in the compositions of the present invention can vary between 0.001% and 10% by weight, calculated to the total composition.

Composition of the present invention may be comprised in a kit and therefore further object of the present invention is a kit comprising composition of the present invention and preferably one or more additional compositions wherein at least one of the is an alkaline composition comprising an alkalizing agent. Furthermore, the composition may be comprised in a kit for bleaching hair wherein the kit comprises composition of the present invention and an anhydrous composition preferably in a powder form.

The following examples are to illustrate the invention but not to limit it.

EXAMPLE 1

|  | % by weight |
| --- | --- |
| Hydrogen peroxide | 12.5 |
| Sucrose | 50.0 |
| Phosphoric acid | q.s. to pH 3.0 |
| Water | to 100 |

The above composition was mixed with an alkaline composition at a weight ratio of 1 to 2 prior to application onto hair streaks. The resulting composition had a pH of 9.9±0.1.

The alkaline composition is as follows:

|  | % by weight |
| --- | --- |
| Ammonia | 10.5 |
| Cetetearyl alcohol | 10.0 |
| Sodium cetearyl sulphate | 4.0 |
| Water | to 100 |

The mixture was applied onto level 3 hair streak and left on the hair for 30 min at 40° C. and rinsed off from the streak with water and streak was shampooed once and dried with a drier. The streak colour intensity (L value) was measured with a laboratory colorimeter. It was observed that the streak treated with the above inventive composition was bleached at a much higher extent than hair streak bleached with comparative composition not comprising sucrose (replaced with water).

The following results were observed

|  | L value |
| --- | --- |
| Inventive composition | 13.99 |
| Comparative composition | 9.51 |

EXAMPLE 2

|  | % by weight |
| --- | --- |
| Hydrogen peroxide | 12.5 |
| PEG-32 | 50.0 |
| Phosphoric acid | q.s. to pH 3.0 |
| Water | to 100 |

The above composition was mixed with an alkaline composition of Example 1 at a weight ratio of 1 to 2 prior to application onto hair streaks. The resulting composition had a pH of 9.9±0.1.

The mixture was applied onto level 3 hair streak and left on the hair for 30 min at 40° C. and rinsed off from the streak with water and streak was shampooed once and dried with a drier. The streak colour intensity (L value) was measured with a laboratory colorimeter. It was observed that the streak treated with the above inventive composition was bleached at a much higher extent than hair streak bleached with comparative composition not comprising PEG-32 (replaced with water).

The following results were observed

|  | L value |
| --- | --- |
| Inventive composition | 14.92 |
| Comparative composition | 9.51 |

Similar results were observed with the following examples.

EXAMPLE 3

|  | % by weight |
| --- | --- |
| Hydrogen peroxide | 12.5 |
| Sucrose | 25.0 |
| PEG-32 | 25.0 |
| Phosphoric acid | q.s. to pH 3.0 |
| Water | to 100 |

The above composition was mixed with an alkaline composition of Example 1 at a weight ratio of 1 to 2 prior to application onto hair streaks. The resulting composition had a pH of 9.9±0.1.

EXAMPLE 4

The oxidizing composition of example 1 was mixed with the following alkalizing composition at a weight ratio of 1:1 prior to application onto hair.

|  | % by weight |
| --- | --- |
| Monoethanolamine | 5.5 |
| Cetetearyl alcohol | 10.0 |
| Sodium cetearyl sulphate | 4.0 |
| Water | to 100 |

It was observed that the hair streak of level 6 was effectively bleached.

EXAMPLE 5

The oxidizing composition of example 2 was mixed with the following alkalizing composition at a weight ratio of 1:1 prior to application onto hair.

|  | % by weight |
| --- | --- |
| Monoethanolamine | 5.5 |
| Cetetearyl alcohol | 10.0 |
| Sodium cetearyl sulphate | 4.0 |
| Water | to 100 |

It was observed that the hair streak of level 6 was effectively bleached.

EXAMPLE 6

The oxidizing composition of example 3 was mixed with the following alkalizing composition at a weight ratio of 1:1 prior to application onto hair.

|  | % by weight |
| --- | --- |
| Monoethanolamine | 5.5 |
| Cetetearyl alcohol | 10.0 |
| Sodium cetearyl sulphate | 4.0 |
| Basic red 51 | 0.5 |
| Water | to 100 |

It was observed that the hair streak of level 6 was effectively bleached and homogeneously coloured into red.

EXAMPLE 7

The oxidizing composition of example 3 was mixed with the following alkalizing composition at a weight ratio of 1:1 prior to application onto hair.

|  | % by weight |
| --- | --- |
| Ammonia | 9.0 |
| Cetetearyl alcohol | 10.0 |
| Cetrimonium chloride | 4.0 |
| Basic yellow 87 | 0.25 |
| Basic red 51 | 0.15 |
| Basic orange 31 | 0.8 |
| Water | to 100 |

It was observed that the hair streak of level 6 was homogeneously orange coloured.

EXAMPLE 8

The oxidizing composition of example 3 was mixed with the following alkalizing composition at a weight ratio of 1:1 prior to application onto hair.

|  | % by weight |
| --- | --- |
| Ammonia | 4.0 |
| Monoethanolamine | 2.5 |
| Cetetearyl alcohol | 10.0 |
| Cetrimonium chloride | 4.0 |
| Basic yellow 87 | 0.25 |
| Basic red 51 | 0.15 |
| Basic orange 31 | 0.8 |
| Water | to 100 |

It was observed that the hair streak of level 6 was homogeneously orange coloured.

EXAMPLE 9

The oxidizing composition of example 3 was mixed with the following powder bleaching composition at a weight ratio of 1:1 prior to application onto hair.

|  | % by weight |
| --- | --- |
| Sodium persulphate | 20.0 |
| Ammonium persulphate | 20.0 |
| Sodium metasilicate | 10.0 |
| Paraffin oil | 8.5 |
| Hydroxyethylcellulose | 5.0 |
| Diatomaceous earth | 36.5 |

The hair streak was homogeneously bleached.

EXAMPLE 10

The oxidizing composition of example 3 was mixed with the following powder bleaching/colouring composition at a weight ratio of 1:1 prior to application onto hair.

|  | % by weight |
| --- | --- |
| Sodium persulphate | 20.0 |
| Ammonium persulphate | 20.0 |
| Sodium metasilicate | 10.0 |
| Paraffin oil | 8.5 |
| Hydroxyethylcellulose | 5.0 |
| Acid red 92 | 1.5 |
| Diatomaceous earth | 35.0 |

The hair streak was homogeneously bleached and coloured into red.

EXAMPLE 11

The oxidizing composition of example 3 was mixed with the following anhydrous paste bleaching composition at a weight ratio of 1:1 prior to application onto hair.

|  | % by weight |
| --- | --- |
| Sodium persulphate | 20.0 |
| Ammonium persulphate | 20.0 |
| Sodium metasilicate | 10.0 |
| Paraffin oil | 28.5 |
| Hydroxyethylcellulose | 5.0 |
| Diatomaceous earth | 16.5 |

The hair streak was homogeneously bleached.

The invention claimed is:

1. An aqueous composition comprising:
   (a) one or more oxidizing agents present at a concentration in a range of 1 to 25% by weight, calculated to a total weight of the aqueous composition; and
   (b) at least one of one or more mono and/or disaccharides and one or more polyethylene glycols, wherein the one or more mono and/or disaccharides, when present in the aqueous composition, is selected from the group consisting of glucose, fructose, mannose, rhamnose, ribose, xylose, lactose, lactulose, maltose, mellibiose, sucralose, sucrose, trehalose, xylobiose, and their mixtures, and present at a concentration in a range of 5 to 60% by weight, calculated to the total weight of the aqueous composition, and the one or more polyethylene glycols, when present in the aqueous composition, is selected from at least one compound according to the general structure $H(OCH_2CH_2)_nOH$, wherein n is 4 to 800, is present at a concentration in a range of 5 to 60% by weight, calculated to the total weight of the aqueous composition, and is selected from the group consisting of PEG-4, PEG-6, PEG-7, PEG-8, PEG-9, PEG-10, PEG-12, PEG-14, PEG-16, PEG-18, PEG-20, PEG-32, PEG-33, PEG-40, PEG-45, PEG-55, PEG-60, PEG-75, PEG-80, PEG-90, PEG-100, PEG-135, PEG-150, PEG-180, PEG-200, PEG-220, PEG-240, PEG-300, PEG-400, PEG-450, PEG-500, PEG-800, and a mixture thereof,
   wherein
   the aqueous composition is configured to be applied onto hair, has a pH between 1 and 5, is free of an alkalizing agent, and is in the form of a solution, emulsion, cream, or mousse.

2. The aqueous composition according to claim 1, wherein the component (a) is selected from the group consisting of hydrogen peroxide, urea peroxide, melamin peroxide and perborate salts.

3. The aqueous composition according to claim 1, wherein the range of the component (a) is 1 to 15% by weight, calculated to the total weight of the aqueous composition.

4. The aqueous composition according to claim 1, having a pH in the range of 1.5 to 4.5.

5. The aqueous composition according to claim 1, further comprising:
   at least one surfactant selected from the group consisting of non-ionic, cationic and anionic surfactants.

6. The aqueous composition according to claim 1, further comprising:
   one or more fatty alcohol and/or oil.

7. A process for bleaching and/or coloring hair, the process comprising:
   (1) mixing, to produce a mixture, an aqueous composition with
      (i) a composition comprising one alkalizing agent, or
      (ii) an anhydrous composition comprising one or more persalt and one or more alkalizing agent, or
      (iii) a composition comprising one or more alkalizing agent and one or more hair dye;
   (2) at least one of bleaching and coloring hair by applying the mixture obtained from (1) onto the hair; and
   (3) after leaving the mixture on the hair for 1 to 60 min, rinsing the mixture off the hair,
   wherein
   the aqueous composition obtained in (1) comprises:
      (a) one or more oxidizing agents present at a concentration in a range of 1 to 25% by weight, calculated to a total weight of the aqueous composition; and
      (b) at least one of one or more mono and/or disaccharides and one or more polyethylene glycols,
      wherein
      the one or more mono and/or disaccharides, when present in the aqueous composition, is selected from the group consisting of glucose, fructose, mannose, rhamnose, ribose, xylose, lactose, lactulose, maltose, mellibiose, sucralose, sucrose, trehalose, xylobiose, and their mixtures, and present at a total concentration in the range of 5 to 60% by weight, calculated to the total weight of the aqueous composition,
      the one or more polyethylene glycols, when present in the aqueous composition, is selected from at least one compound according to the general structure $H(OCH_2CH_2)_nOH$, wherein n is 4 to 800, is present at a concentration in a range of 5 to 55% by weight, calculated to the total weight of the aqueous composition, and is selected from the group consisting of PEG-4, PEG-6, PEG-7, PEG-8, PEG-9, PEG-10, PEG-12, PEG-14, PEG-16, PEG-18, PEG-20, PEG-32, PEG-33, PEG-40, PEG-45, PEG-55, PEG-60, PEG-75, PEG-80, PEG-90, PEG-100, PEG-135, PEG-150, PEG-180, PEG-200, PEG-220, PEG-240, PEG-300, PEG-400, PEG-450, PEG-500, PEG-800, and a mixture thereof, and
      the aqueous composition has a pH between 1 and 5 and is free of one at least one selected from an alkalizing agent and an oxidative dye precursor.

8. The aqueous composition according to claim 1, wherein the component (b) is present at a total concentration in the range of 10 to 60% by weight, calculated to the total weight of the aqueous composition.

9. The aqueous composition according to claim 8, wherein the component (b) is present at a total concentration in the range of 15 to 60% by weight, calculated to the total weight of the aqueous composition.

10. The aqueous composition according to claim 1, wherein the form of the aqueous composition is selected from an emulsion, a cream, or a mousse.

11. The aqueous composition according to claim 8, wherein the form of the aqueous composition is selected from an emulsion, a cream, or a mousse.

* * * * *